US011369275B2

(12) United States Patent
Song et al.

(10) Patent No.: US 11,369,275 B2
(45) Date of Patent: Jun. 28, 2022

(54) DEVICE FOR READ-OUT OF A PHOTOPLETHYSMOGRAPHY SIGNAL AND A WEARABLE SENSOR

(71) Applicants: IMEC VZW, Leuven (BE); STICHTING IMEC NEDERLAND, AE Eindhoven (NL)

(72) Inventors: Shuang Song, Leuven (BE); Jiawei Xu, Leuven (BE); Roland Van Wegberg, Leuven (BE); Nick Van Helleputte, Leuven (BE)

(73) Assignees: IMEC VZW, Leuven (BE); STICHTING IMEC NEDERLAND, AE Eindhoven (NL)

( * ) Notice: Subject to any disclaimer, the term of this patent is extended or adjusted under 35 U.S.C. 154(b) by 188 days.

(21) Appl. No.: 16/709,908

(22) Filed: Dec. 10, 2019

(65) Prior Publication Data
US 2020/0187788 A1 Jun. 18, 2020

(30) Foreign Application Priority Data
Dec. 14, 2018 (EP) .................................... 18212678

(51) Int. Cl.
*A61B 5/0295* (2006.01)
*A61B 5/0205* (2006.01)
(Continued)

(52) U.S. Cl.
CPC .......... *A61B 5/0205* (2013.01); *A61B 5/0295* (2013.01); *A61B 5/14552* (2013.01);
(Continued)

(58) Field of Classification Search
CPC . A61B 5/0205; A61B 5/0295; A61B 5/14552; A61B 5/681; A61B 5/02427;
(Continued)

(56) References Cited

U.S. PATENT DOCUMENTS 5,561,288 A 10/1996 Stevens
6,261,236 B1 7/2001 Grinsblatov
(Continued)

FOREIGN PATENT DOCUMENTS

EP 0666657 A1 8/1995

OTHER PUBLICATIONS

Sun et al: "Photoplethysmography revisited: from contact to noncontact, from point to imaging", IEEE Transactions on Biomedical Engineering, 2016, vol. 63, No. 3, pp. 463-477.
(Continued)

*Primary Examiner* — Joseph M Dietrich
*Assistant Examiner* — Michael T. Holtzclaw
(74) *Attorney, Agent, or Firm* — Moser Taboada (57) ABSTRACT

A device for read-out of a photoplethysmography (PPG) signal comprises: a photodiode, which is configured to detect a PPG signal, the photodiode comprising a first and a second terminal; and a read-out circuitry for reading out the PPG signal, wherein an input stage is connected to receive a first and a second input signal from the terminals and a DC bias voltage, and wherein the input stage is configured for current sensing to provide a fully differential amplification of the input signals to a first and a second current signal, and wherein an output stage is configured to receive the current signals, wherein the current signals comprise an AC and a DC component of the PPG signal, and wherein the output stage is configured to generate a differential output voltage through a gain component.

14 Claims, 5 Drawing Sheets

(51) Int. Cl.
*A61B 5/1455* (2006.01)
*A61B 5/00* (2006.01)
*A61B 5/024* (2006.01)

(52) U.S. Cl.
CPC .......... *A61B 5/681* (2013.01); *A61B 5/02427* (2013.01); *A61B 5/02438* (2013.01)

(58) Field of Classification Search
CPC ............ A61B 5/02438; A61B 5/14551; A61B 5/7225; A61B 5/02416; H03F 3/45179; H03F 3/08
See application file for complete search history.

(56) References Cited

U.S. PATENT DOCUMENTS

| | | |
|---|---|---|
| 6,307,196 B1 | 10/2001 | Thompson et al. |
| 6,323,734 B1 | 11/2001 | Henrion et al. |
| 6,359,517 B1 | 3/2002 | Colaco |
| 2001/0050333 A1 | 12/2001 | Feng et al. |
| 2009/0194672 A1 | 8/2009 | Tredwell et al. |
| 2014/0323844 A1 | 10/2014 | Deliwala et al. |
| 2015/0086221 A1 | 3/2015 | Shringarpure et al. |
| 2020/0205680 A1* | 7/2020 | Boukhayma ......... A61B 5/7225 |

OTHER PUBLICATIONS

Extended European Search Report in EP18212678.9 dated Jun. 17, 2019.

* cited by examiner

DEVICE FOR READ-OUT OF A PHOTOPLETHYSMOGRAPHY SIGNAL AND A WEARABLE SENSOR

CROSS-REFERENCE TO RELATED APPLICATION

The present application is based on priority claimed on European Patent Application No. 18212678.9, filed on Dec. 14, 2018, the contents of which are incorporated herein by reference.

TECHNICAL FIELD

The present inventive concept relates to a device for read-out of a photoplethysmography (PPG) signal. In particular, the present inventive concept relates to a read-out circuitry for acquiring a PPG signal.

The present inventive concept also relates to a wearable sensor, in which the device for read-out of a PPG signal is arranged.

BACKGROUND ART

Acquisition of signals representing a heart activity of a subject is important or of interest in many contexts. The signals may be used in clinical settings to provide information for treatment of the subject, but may also be used for general monitoring of a physical condition of the subject. Also, monitoring of heart activity may be of interest to the subject, e.g. for monitoring exercise or other activities of the subject. Photoplethysmography is a technology of interest in monitoring heart activity as it may be provided in a wearable device which may minimally affect a comfort of the subject wearing the device.

However, a photoplethysmogram (PPG) signal may be affected by motion artifacts, which can introduce a larger amplitude than the PPG signal. Thus, if the subject is moving, motion artifacts may be generated which may cause quality of an acquired PPG signal to deteriorate or may prevent making any assessments based on the PPG signal. This is accentuated, when the PPG signal is acquired during daily life of a subject.

Motion artifacts in the PPG signal may have a large amplitude. Thus, it would be desirable that read-out circuitry for reading out the PPG signal provides a high dynamic range.

In U.S. Pat. No. 5,561,288 a highly sensitive optical receiver is disclosed where one terminal of a photodiode of the receiver is connected to a negatively biased amplifier while the other terminal of photodetector is connected to a positively biased amplifier, where such connections automatically bias the photodiode and use the current from both terminals (anode and cathode) of the photodiode. The optical receiver further has a DC cancellation circuit to eliminate the biasing voltages in the final output signal.

Amplifiers connected to both terminals of a photodiode may allow an improved dynamic range in detecting a photodiode signal. However, since a DC cancellation circuit is used for eliminating biasing voltages, the receiver circuitry prevents detection of DC components of the photodiode signal. This prevents detection of a DC component of a PPG signal, which may provide information of the physical condition of the subject.

Thus, it would be desirable to provide read-out of a PPG signal using a high dynamic range while enabling DC components of the PPG signal to be detected.

SUMMARY

An objective of the present inventive concept is to provide a read-out of PPG signals, which may enable acquiring PPG signals with a high dynamic range, while maintaining a DC component of the PPG signal.

This and other objectives of the invention are at least partly met by the invention as defined in the independent claims. Preferred embodiments are set out in the dependent claims.

According to a first aspect, there is provided a device for read-out of a photoplethysmography (PPG) signal, said device comprising: a photodiode, which is configured to detect a PPG signal as intensity of light based on interaction of an emitted light signal with a blood flow of a subject, the photodiode comprising a first and a second terminal on opposite sides of the photodiode; and a read-out circuitry for reading out the PPG signal detected by the photodiode, the read-out circuitry comprising an input stage and an output stage; wherein the input stage is connected to receive a first input signal from the first terminal of the photodiode, a second input signal from the second terminal of the photodiode, and a DC bias voltage, and wherein the input stage is configured for current sensing to provide a fully differential amplification of the first input signal and the second input signal to a first current signal and a second current signal, and wherein the output stage is configured to receive the first current signal and the second current signal, wherein the first current signal and the second current signal comprise an AC component and a DC component of the PPG signal, and wherein the output stage is configured to generate a differential output voltage through a gain component.

The device is configured to provide a fully differential amplification of the first and second input signal from the photodiode. This implies that a high dynamic range of the read-out circuitry may be provided.

Further, the input stage is connected to receive a DC bias voltage. Thus, the photodiode may be set to be reverse biased. A reverse bias of the photodiode may reduce a response time of the photodiode compared to a photodiode with zero bias (in a photovoltaic mode).

Thus, the device may enable read-out of a PPG signal with a short settling time. This may be particularly advantageous as the PPG signal may be acquired based on short pulses of light from a light-emitting diode (LED). Hence, power consumption of a LED for emitting light in order to enable PPG signal acquisition may be limited. Since the device may typically be used for being worn by a subject, power consumption may be important in order to reduce need of recharging a battery.

The input stage of the device is configured for current sensing to provide a first current signal and a second current signal, which are received by the output stage. Thanks to the use of current sensing, the device enables the photodiode signal to be sensed without being affected by the DC bias voltage.

The current sensing for each current signal may be provided by a current sensor being included in a feedback loop of an amplifier. Further, the bias voltage may be provided at a positive input of the amplifier. This implies that a DC bias for the photodiode may be provided without interfering with detection of the photodiode signal through the current sensor. Hence, the device may enable detection of a DC component which is not affected by a DC bias. Thus, the device may provide read-out of a PPG signal for providing a differential output voltage with an AC component and a DC component without a DC bias voltage appearing in the differential output voltage.

The device may allow acquiring of a PPG signal with a high dynamic range through the using of a fully differential amplification. The device may further provide a fast response time allowing use of short LED pulses by providing a DC bias of the photodiode. Further, thanks to arrangement of current sensing, the DC bias need not affect the acquired signal such that both AC component and DC component of the PPG signal may be acquired.

The read-out circuitry may be provided integrated in a chip, such as being part of a system-on-a-chip (SoC). This may facilitate arranging the read-out circuitry in different apparatuses, which may also include the photodiode and a LED for emitting light in order to enable PPG signal acquisition. Thus, the SoC may for instance be embedded in a wearable sensor, but it may alternatively be arranged in a non-wearable apparatus, which may for instance be used in a hospital for acquiring a PPG signal.

According to an embodiment, the input stage comprises a first differential amplifier, which comprises a first and a second input of the first differential amplifier connected to receive the first input signal and the DC bias voltage, respectively, and which is configured to output an amplified signal to a first current sensor for generating the first current signal, and wherein the input stage comprises a second differential amplifier, which comprises a first and a second input of the second differential amplifier connected to receive the second input signal and the DC bias voltage, respectively, and which is configured to output an amplified signal to a second current sensor for generating the second current signal.

Thus, the input stage may be configured to provide differential amplification by means of a first and a second differential amplifier connected to the first and the second terminal of the photodiode, respectively.

According to an embodiment, the first differential amplifier comprises a feedback loop connecting the first current sensor to the first input of the first differential amplifier, and wherein the second differential amplifier comprises a feedback loop connecting the second current sensor to the first input of the second differential amplifier.

A signal current may be sensed through the feedback loops of the differential amplifier and the photodiode. The first and second current sensors may be configured to detect the signal current, which may enable the signal current to be provided to the output stage.

The first and the second differential amplifier may each be connected to the DC bias voltage at a positive input of each of the first and the second differential amplifier. The bias voltage may then be provided to the terminals of the photodiode by the feedback loop.

According to this embodiment, a DC bias for the photodiode may be suitably provided without interfering with detection of the photodiode signal through the first and second current sensors.

According to an embodiment, the output stage comprises a first current source, which is controlled by the first current signal, and a second current source, which is controlled by the second current signal.

The first and the second current source may ensure that a signal current forming a copy of a signal current through the photodiode may be provided at the output stage. The copied signal current may thus be advantageously used for generating a differential output voltage which enables detection of both AC component and DC component of the PPG signal.

According to an embodiment, the gain component of the output stage comprises a resistor for providing a transimpedance amplifier mode of the output stage.

The transimpedance amplifier may provide a current to voltage converter for converting the sensed current signals to an output voltage.

A transimpedance amplifier may present a low impedance to the photodiode and isolate the photodiode from an output voltage of the transimpedance amplifier.

According to an embodiment, the gain component of the output stage comprises a capacitor for providing an integration mode of the output stage.

The integration mode may provide a low-pass filter of the device, which may be useful for filtering out high frequencies from the PPG signal.

According to an embodiment, the output stage is configured to be selectively set in a transimpedance amplifier mode or an integration mode.

Thus, the output stage may be dynamically controlled in order to switch an operation mode of the device, e.g. based on conditions for reading the PPG signal. This increases versatility of the device.

According to a second aspect, there is provided a wearable sensor for acquiring physiological information through a photoplethysmography (PPG) signal, the wearable sensor comprising: a carrier, which is configured to be worn by a subject; a light emitting diode (LED), which is configured to emit a light signal; a device according to any one of the preceding claims; wherein the carrier is configured to carry the LED and the device such that, when the carrier is worn by the subject, the LED is arranged to emit a light signal towards a skin of the subject and the photodiode of the device is arranged to detect the PPG signal as intensity of light based on interaction of the emitted light signal with a blood flow of the subject.

Effects and features of this second aspect are largely analogous to those described above in connection with the first aspect. Embodiments mentioned in relation to the first aspect are largely compatible with the second aspect.

Thus, a wearable sensor for acquiring a PPG signal may be provided with a device which enables a high dynamic range of the acquired signal. Thus, the wearable sensor may provide a useful PPG signal in relation to large amplitude motion artifacts, which is especially advantageous as a wearable sensor may be relatively prone to be exposed to motion artifacts.

Further, the read-out of the PPG signal may provide a short settling time, which may allow use of short light pulses by the LED while still allowing a high quality PPG signal to be acquired. This may ensure that a power consumption of the LED is limited, which is very useful in the wearable sensor, e.g. because re-charging of a battery may need to be performed less frequently, improving usability of the wearable sensor.

According to an embodiment, the LED is configured to emit green light.

A PPG signal based on a green light may provide a relatively large ratio between AC and DC components. Hence, using the device for read-out of the PPG signal for reading out a PPG signal based on emitted green light may enable representing the AC components of the PPG signal with high accuracy, while the dynamic range of the reading out of the PPG signals allows detection of both DC and AC level of the PPG signal.

It should be realized that the wearable sensor may alternatively or additionally be provided with a LED that is configured to emit red light and/or a LED that is configured to emit infrared light.

Detection of the PPG signal may benefit from a high dynamic range regardless of a wavelength used for detecting the PPG signal. Different wavelengths may be used for different types of analysis of the PPG signal. For instance, green light may typically be used in detection of a heart rate from the PPG signal, whereas red light and/or infrared light may typically be used for determining blood oxygen saturation based on the PPG signal.

According to an embodiment, the carrier is configured to carry the LED and the photodiode of the device such that, when the carrier is worn by the subject, the photodiode is configured to detect light emitted by the LED that is reflected by blood flow of the subject.

A PPG signal acquired in reflection mode may provide a stronger signal than a PPG signal acquired in transmissive mode. This implies that a smaller intensity of light may be used, such that power consumption of the wearable sensor may be limited. Further, a large ratio between AC and DC components of the PPG signal may enable representing the AC components of the PPG signal with high accuracy, while the dynamic range of the reading out of the PPG signals allows detection of both DC and AC level of the PPG signal.

However, it should be realized that the wearable sensor may alternatively be configured to carry the LED and the photodiode of the device such that, when the carrier is worn by the subject, the photodiode is configured to detect light emitted by the LED that is transmitted through blood flow of the subject. For instance, the LED and the photodiode may be arranged at opposite sides of a carrier being configured to be worn around a body part of the subject, such as around a wrist or a finger of the subject.

According to an embodiment, the wearable sensor further comprises LED driving circuitry, which is configured to control the LED to emit pulsed light.

Thus, the wearable sensor may be configured to control the LED such that light pulses may be emitted for acquiring the PPG signal. Since the device for read-out of the PPG signal may have a short settling time, the LED driving circuitry may control the LED to emit short pulses of light, such that a power consumption of the wearable sensor may be limited.

According to an embodiment, the wearable sensor further comprises a processor, which is configured to receive a processor input signal based on the differential output voltage from the output stage of the read-out circuitry and which is configured to process the processor input signal for determining physiological information based on the processor input signal.

Thus, the wearable sensor may comprise a processor such that physiological information may be determined within the wearable sensor. However, it should be realized that the wearable sensor may alternatively transfer a read out PPG signal to an external processor, which may be arranged in any external apparatus.

According to an embodiment, the processor is configured to determine an estimated heart rate based on the PPG signal.

Thus, the PPG signal may allow determining a heart rate of a subject. This implies that the wearable sensor may provide determination of a heart rate, while not affecting daily life of a subject as the wearable sensor may e.g. be worn around a wrist of the subject.

According to an embodiment, the processor is configured to determine an estimated blood oxygen saturation.

Determination of blood oxygen saturation may typically include calculating a first ratio of AC component to DC component for the PPG signal based on red light and a second ratio of AC component to DC component for the PPG signal based on IR light and then determining a ratio of the first ratio to the second ratio. Thus, determination of blood oxygen saturation may require detecting both an AC component and a DC component of a PPG signal. Hence, the device for read-out of the PPG signal is especially suited for detecting a PPG signal such that blood oxygen saturation may be estimated, since the DC component of the PPG signal is maintained.

According to an embodiment, the wearable sensor may further comprise a signal pre-processing unit, which is configured to receive a differential output voltage signal from the read-out circuitry and to pre-process the differential output signal by filtering the signal and analog-to-digital converting the signal.

Thus, the wearable sensor may be configured to process the differential output voltage signal to provide a digital representation of the PPG signal, which may facilitate further processing of the PPG signal, such as making analyses based on the PPG signal.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Detailed embodiments of the present inventive concept will now be described with reference to the drawings.

Figure 1:
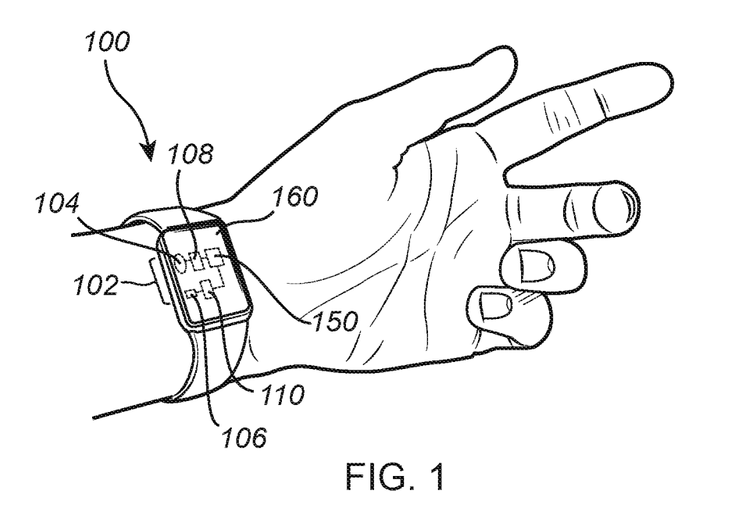
FIG. 1 is a schematic view of a wearable sensor according to an embodiment.

Referring now to FIG. 1, a wearable sensor 100 for acquiring and processing a photoplethysmography (PPG) signal will be generally described.

The wearable sensor 100 may comprise a PPG detector 102. The PPG detector 102 may comprise a light source 104 and a light sensor 106 for detecting an intensity of light. The light source 104 and the light sensor 106 may be arranged on opposite sides of tissue, such as a fingertip, for acquiring an intensity of light transmitted through the tissue, so called transmittance-type PPG. However, the light source 104 and the light sensor 106 may alternatively be arranged on a common side of tissue for acquiring an intensity of light diffusely reflected by the tissue, so called reflectance-type PPG. Reflectance-type PPG may be advantageously used, because it may facilitate arranging the PPG detector 102 in a wrist-worn device, such as in a smart watch or bracelet, or in an adhesive patch which may e.g. be attached to a chest of a person.

The light source 104 may be provided in form of a light emitting diode (LED). A LED may enable an accurate control of light emitted by the light source 104 and may output light of a desired wavelength for receiving a desired response from the tissue.

The light source 104 may be connected to a driving circuitry 108, which may control the light source 104 to output light.

The driving circuitry 108 may need to provide a current in an order of 10 mA in order to drive the LED 104 to emit light of such an intensity that the light penetrates skin and tissue so as to enable detecting a PPG signal from interaction of light with blood flow. This implies that power consumption for driving the LED 104 may constitute a major portion of power consumed by a wearable sensor 100.

In order to reduce power consumption, the driving circuitry 108 may control the LED 104 to emit light pulses. However, noise folding puts a limit to reduction of a repetition frequency of emitted pulses. Thus, in order to further reduce power consumption of the wearable sensor 100, a pulse length of the emitted light pulses should be reduced. This, on the other hand, requires a fast settling time of a read-out circuitry for reading out a signal from the light sensor 106.

The light sensor 106 may be provided in form of a photodiode 106, which is configured to generate a signal based on amount of light incident on the photodiode 106.

The wearable sensor 100 may further comprise read-out circuitry 110 for reading out a PPG signal from the photodiode 106, as will be described in further detail below. The read-out circuitry 110 may be adapted to provide a fast settling time so as to enable use of short light pulses by the LED 104.

The wearable sensor 100 may further comprise a processor 150, which is configured to process a signal acquired by the read-out circuitry 110. The processor 150 may be configured to process the signal in order to determine physiological information of a subject wearing the wearable sensor 100. The processor 150 may for instance determine a heart rate of the subject based on the received signal.

The processor 150 may thus provide processed information which may e.g. be further transferred to an external unit or may be output on a display for presentation to the subject.

The processor 150 may be arranged to be carried by a common carrier 160 with the PPG detector 102. The processor 150 may thus be arranged in a unit, which may be worn by the subject, thus allowing acquiring signals and also processing of the signals close to the subject. This may imply that the processing may be performed in real-time and analysis results may be provided directly to the subject, e.g. in a display mounted on the carrier 160.

However, the processor 150 may be arranged in a different unit remote from the carrier 160. Thus, the carrier 160 may be provided with a communication unit, for wired or wireless communication, and may transmit, possibly pre-processed, PPG signals to an external unit housing the processor 150. The external unit may be arranged close to the subject, such as in a computer arranged in a hospital room, when the carrier 160 is worn by a subject receiving hospital care.

However, the external unit may also be very remotely placed. The communication may be over a computer network, such as the Internet, which may also allow the processor 150 to be arranged on any server or computer connected to the network and may hence be said to be provided "in the cloud". The processor 150 may then further be arranged to transmit cleaned PPG signals or extracted features back to a unit close to the subject, or to a communication unit in the carrier 160, e.g. for display of results to the subject.

The processor 150 may be implemented in hardware, or as any combination of software and hardware. At least part of the functionality of the processor 150 may, for instance, be implemented as software being executed on a general-purpose computer. The wearable sensor 100 may thus be used in combination with one or more processing units, such as a central processing unit (CPU), which may execute the instructions of one or more computer programs in order to implement desired functionality.

The processor 150 may alternatively be implemented as firmware arranged e.g. in an embedded system, or as a specifically designed processing unit, such as an Application-Specific Integrated Circuit (ASIC) or a Field-Programmable Gate Array (FPGA).

The processor 160 may be further configured to control the driving circuitry 108 for the LED 104.

According to an embodiment, the carrier 160 may be wearable by the subject. The carrier 160 may thus comprise an adhesive patch for attachment to a skin surface of the subject. The carrier 160 may alternatively comprise a band element or ring-shaped element for attachment around a body part. The carrier 160 could for instance comprise two band parts, which may be attached to each other in an adjustable relationship for fitting the carrier 160 tightly around the body part. This may be used for arranging the carrier 160 around a wrist, a finger or a torso of the subject.

Wrist-worn PPG devices such as smart watches may be used during daily ambulatory activities, which leads to relatively frequent motion artifacts. Motion in daily life can change the ambient light captured by the light sensor 106, the location of the carrier 160 with respect to the wrist, and a pressure between the carrier 160 and skin. All of these changes may cause fluctuations in the detected PPG signals.

Figure 2:
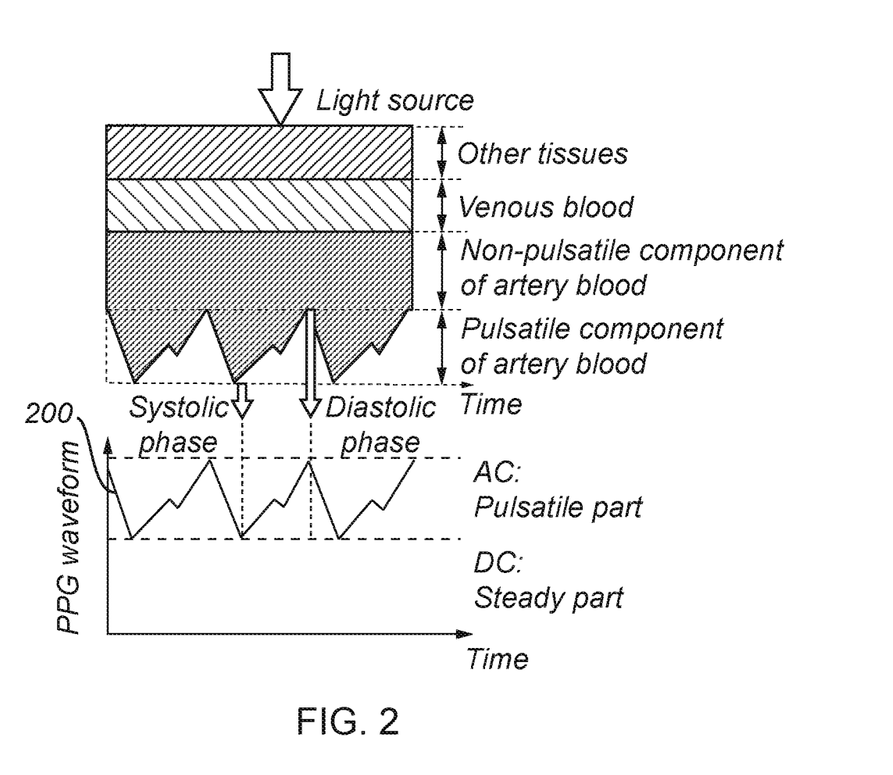
FIG. 2 is a schematic view of a PPG signal illustrating a DC component and an AC component.

FIG. 2 is based on a figure presented in Sun Y., Thakor N., "*Photoplethysmography revisited: from contact to noncontact, from point to imaging*", IEEE Transactions on Biomedical Engineering, 2016, vol. 63, no. 3, pp: 463-477.

As shown in FIG. 2, the detected PPG signal 200 can be split into two components. One component is a DC component which originates from constant absorbance by skin pigmentation, fat, muscle, bone and an average blood volume of arterial and venous blood in the illuminated tissue. The other component is an AC component which originates from the cardiac-induced variations in blood volume that are related to the cardiac rhythm (systole and diastole). The AC component may be mainly used for determining heart activity of a subject, such as for extraction of heart rate, e.g. by detecting peaks in the AC component and determining a frequency of peaks.

A ratio of the AC component to the DC component may be used in estimating blood oxygen saturation of the subject. For instance, blood oxygen saturation may be determined by calculating a first ratio of AC component to DC component for the PPG signal based on red light and a second ratio of AC component to DC component for the PPG signal based on IR light and then determining a ratio of the first ratio to the second ratio. The blood oxygen saturation may thus be estimated based on a pulse modulation ratio R given by:

$$R = \frac{\frac{AC_{red}}{DC_{red}}}{\frac{AC_{IR}}{DC_{IR}}},$$

where red is $AC_{red}$ an amplitude of the AC component for the PPG signal based on red light, $DC_{red}$ is a level of the DC component for the PPG signal based on red light, $AC_{IR}$ is an amplitude of the AC component for the PPG signal based on infrared light, $DC_{IR}$ is a level of the DC component for the PPG signal based on infrared light.

An amplitude of the DC components may vary substantially. Further, it is desired to detect the AC component superposed on the DC component. Also, motion artifacts may cause the signal level to vary substantially. Hence, the dynamic range of the read-out circuitry 110 is preferably large. For instance, a dynamic range of more than 80 dB may be desired.

Figure 3A:
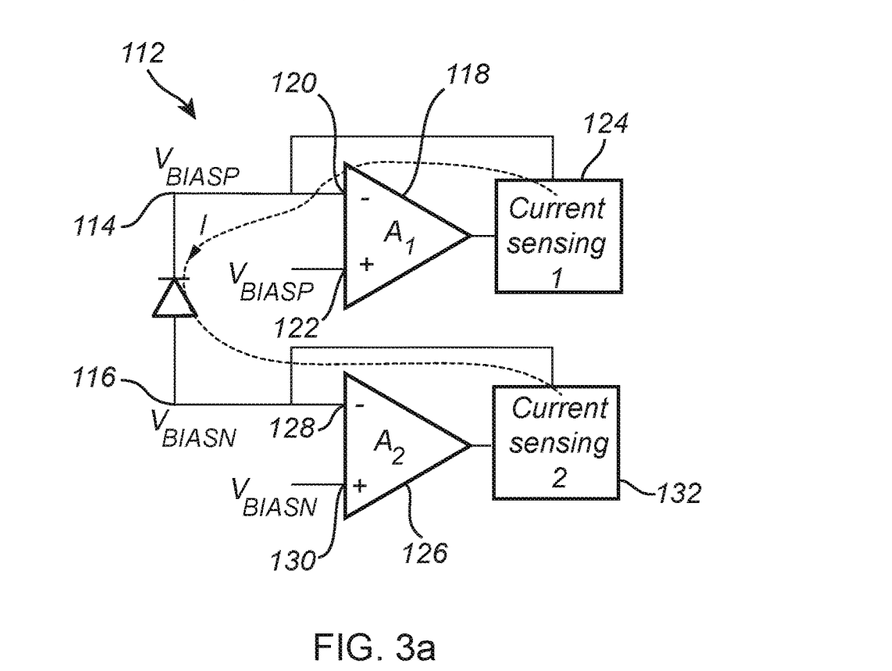
FIG. 3a is a schematic view of an input stage of a read-out circuitry for reading out a PPG signal according to an embodiment.
Figure 3B:
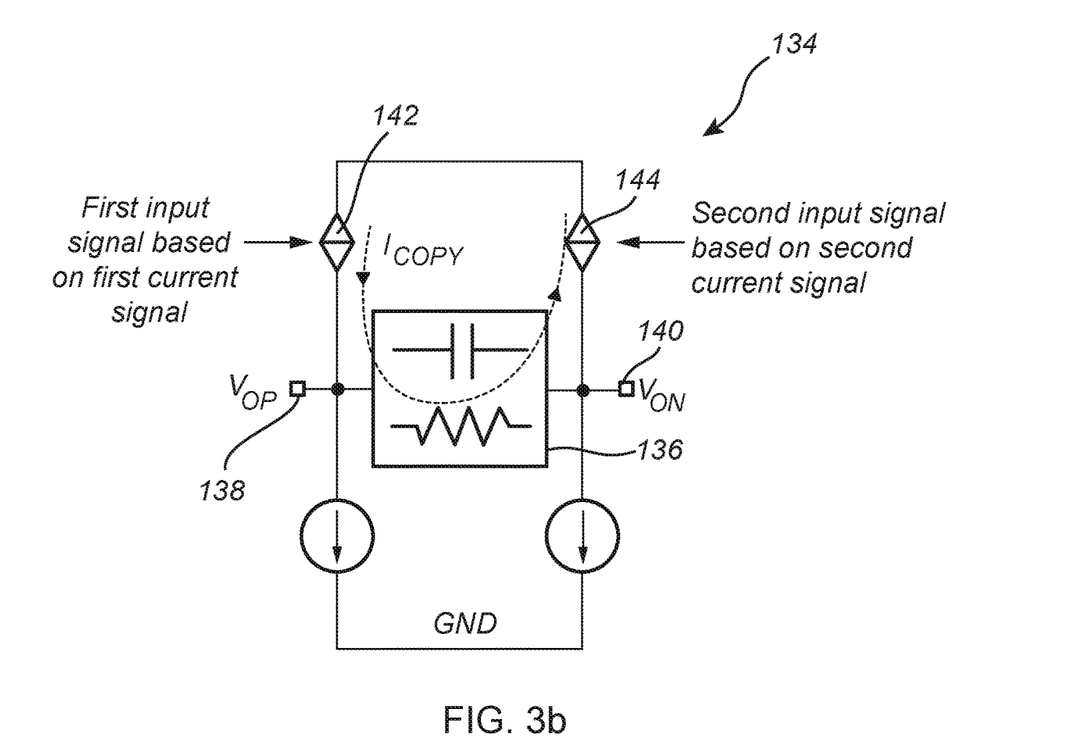
FIG. 3b is a schematic view of an output stage of a read-out circuitry for reading out a PPG signal according to an embodiment.

Referring now to FIGS. 3*a*-*b*, the read-out circuitry 110 for reading out the PPG signal detected by the photodiode 106 will be described in further detail.

The read-out circuitry 110 may comprise an input stage 112 as illustrated in FIG. 3*a* and an output stage 134 as illustrated in FIG. 3*b*.

The input stage 112 may be connected to receive a first input signal from a first terminal 114 of the photodiode 106 and a second input signal from a second terminal 116 of the photodiode 106. Thus, a differential input may be provided to the input stage 112 from the photodiode 106.

The input stage 112 may comprise a first differential amplifier 118, which comprises a first input 120 connected to receive the first input signal and a second input 122 connected to receive a DC bias voltage. The first differential amplifier 118 may be configured to output an amplified signal to a first current sensor 124, which is also connected to a feedback loop of the first differential amplifier 118 for providing a feedback signal to the first input 120.

The input stage 112 may further comprise a second differential amplifier 126, which comprises a first input 128 connected to receive the second input signal and a second input 130 connected to receive the DC bias voltage. The second differential amplifier 126 may be configured to output an amplified signal to a second current sensor 132, which is also connected to a feedback loop of the second differential amplifier 126 for providing a feedback signal to the first input 128.

The signal current I as indicated in FIG. 3*a* is sensed by the first and second current sensors 124, 132. Further, the DC bias voltage for the photodiode 106 is set at positive inputs 122, 130 of the first and the second differential amplifiers 118, 126, such that the DC bias voltage is applied to the first terminal 114 and the second terminal 116 of the photodiode 106 by the feedback loop of the first differential amplifier 118 and the second differential amplifier 126, respectively. The current sensing by the first and second current sensors 124, 132 and the DC biasing of the photodiode 106 may be provided simultaneously without interfering with each other.

The DC biasing of the photodiode 106 may ensure that the photodiode 106 may have a low parasitic capacitance. Further, the input stage 112 may be configured to provide low impedance nodes at the photodiode inputs. This may facilitate that the read-out circuitry 110 enables a fast settling time.

The output stage 134 may be connected to receive a first input signal based on a first current signal generated by the first current sensor 124 and a second input signal based on a second current signal generated by the second current sensor 132. The output stage 134 may be configured to form a copied signal current $I_{copy}$ in the output stage 134.

The output stage 134 may be configured such that the copied signal current $I_{copy}$ may flow through a gain component 136 to generate a differential output voltage $V_{OP}$, $V_{ON}$ at nodes 138, 140.

As shown in FIG. 3*b*, the output stage 134 may comprise a first current source 142 which is controlled by the first current signal and a second current source 144 which is controlled by the second current signal. The current sources 142, 144 may be arranged on opposite sides of the gain component 136 so as to generate a copied signal current $I_{copy}$ through the gain component 136. Instead of the current sources 142, 144, the output stage 134 may alternatively be provided with current sinks.

As schematically illustrated in FIG. 3*b*, the gain component 136 may be configured as a resistor or a capacitor. When the gain component 136 is configured as a resistor, a transimpedance amplifier mode of operation of the output stage 134 is provided. When the gain component 136 is configured as a capacitor, an integration mode of operation of the output stage 134 is provided.

The output stage 134 may be configured to be controlled, such that the output stage 134 may be selectively set in the transimpedance amplifier mode or the integration mode based on a control signal received by the output stage 134. Thus, the read-out circuitry 110 may be dynamically controlled to provide a transimpedance amplifier functionality or an integrator functionality.

Figure 4:
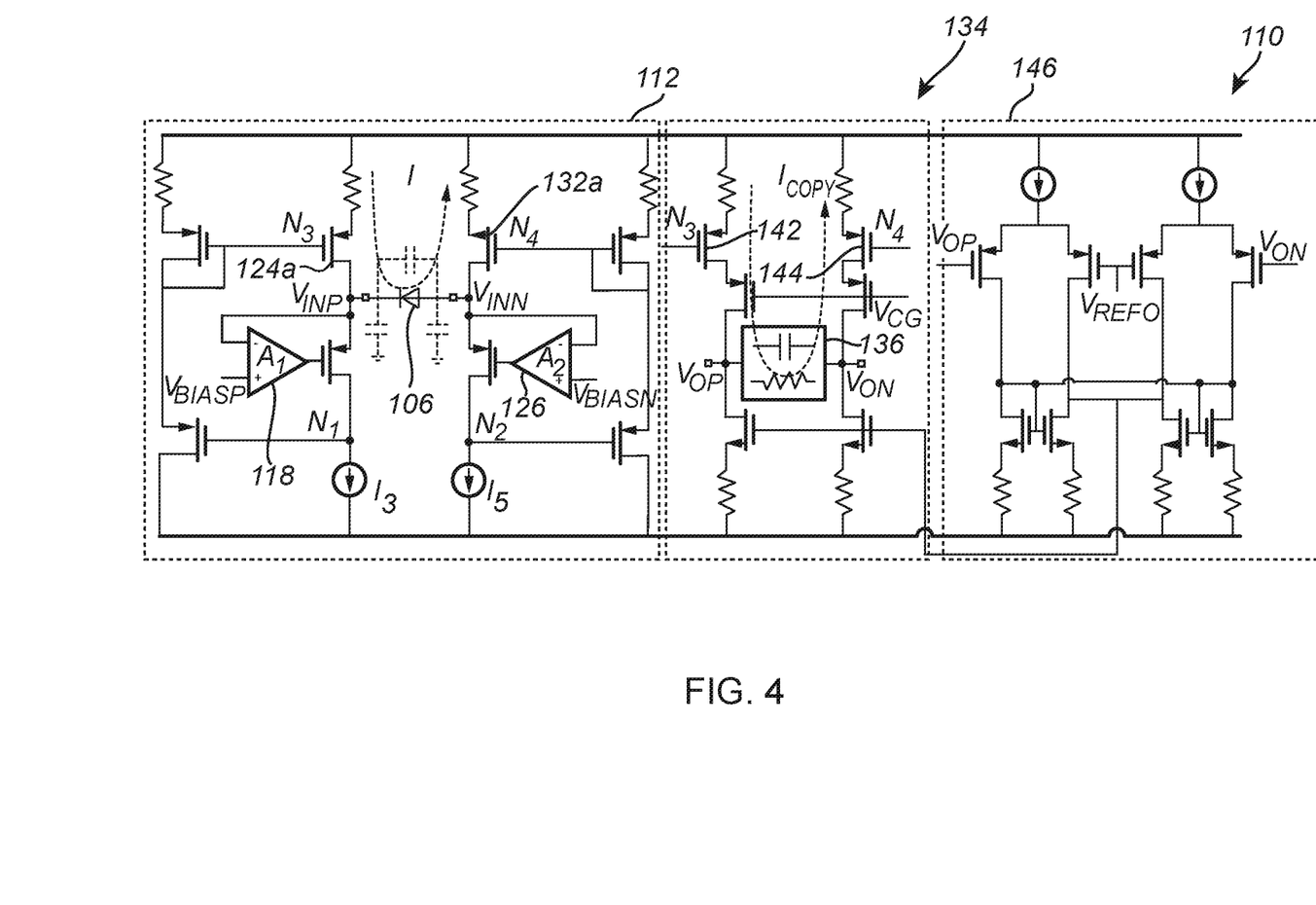
FIG. 4 is a schematic view of a read-out circuitry according to a first embodiment.

Referring now to FIG. 4, a more detailed architecture of the read-out circuitry 110 according to a first embodiment is illustrated.

Here, bias voltages $V_{BIASP}$, and $V_{BIASN}$ are provided to the first differential amplifier 118 and the second differential amplifier 126, respectively, to generate a current I through the photodiode 106. The current passes through transistors 124*a*, 132*a* of the first and second current sensor 124, 132, respectively.

Signals N3 and N4 from the transistors 124*a*, 132*a*, respectively are provided to current sources 142, 144 for generating a copied signal current $I_{copy}$ in the output stage 134 through the gain component 136.

The output stage 134 is further provided with a common mode feedback circuit 146.

Figure 5:
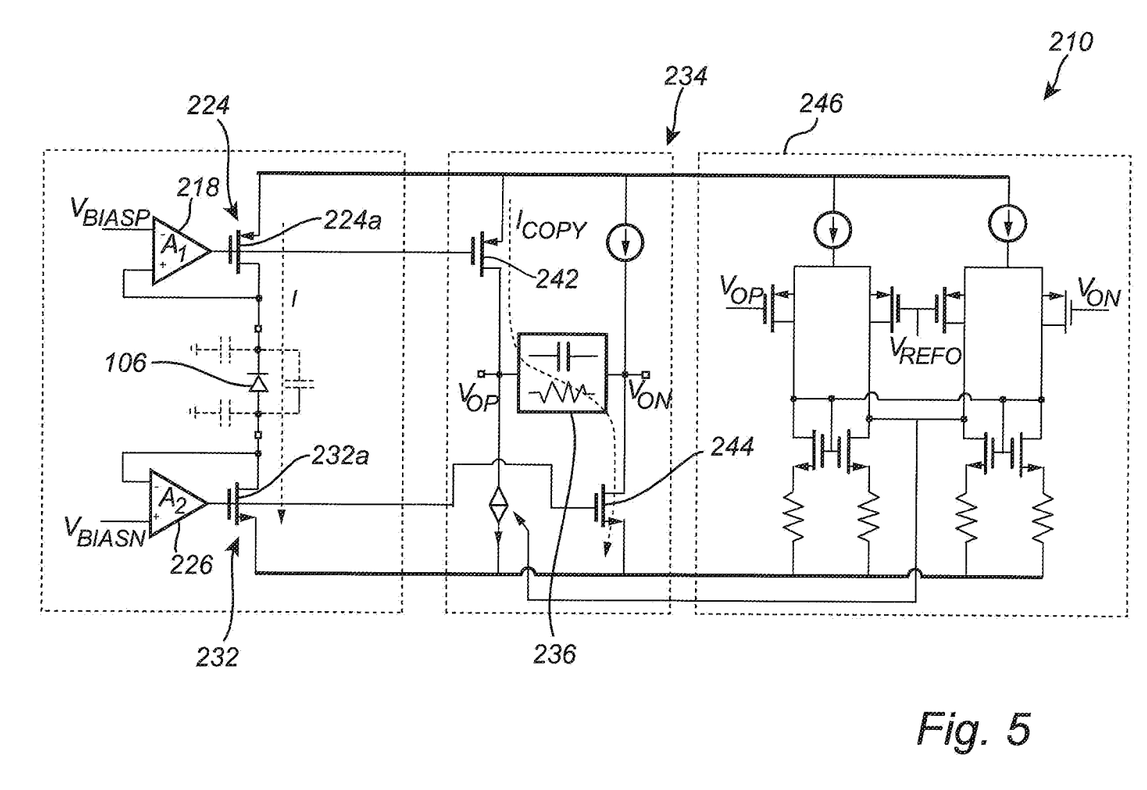
FIG. 5 is a schematic view of a read-out circuitry according to a first embodiment.

Referring now to FIG. 5, a more detailed architecture of the read-out circuitry 210 according to a second embodiment is illustrated.

Here, bias voltages $V_{BIASP}$, and $V_{BIASN}$ are provided to the first differential amplifier 218 and the second differential amplifier 226, respectively, to generate a current I through the photodiode 106. The current passes through transistors 224*a*, 232*a* of the first and second current sensor 224, 232, respectively.

The signal on a gate of the transistor 224*a* is provided to a gate of a first transistor 242 of the output stage 234 and the signal on a gate of the transistor 232*a* is provided to a gate of a second transistor 244 of the output stage 234. The first and second transistors 242, 244 are arranged on opposite sides of the gain component 236 for providing a copied signal current $I_{copy}$ in the output stage 234 through the gain component 236.

Again, the output stage 234 is further provided with a common mode feedback circuit 246.

Figure 6A:
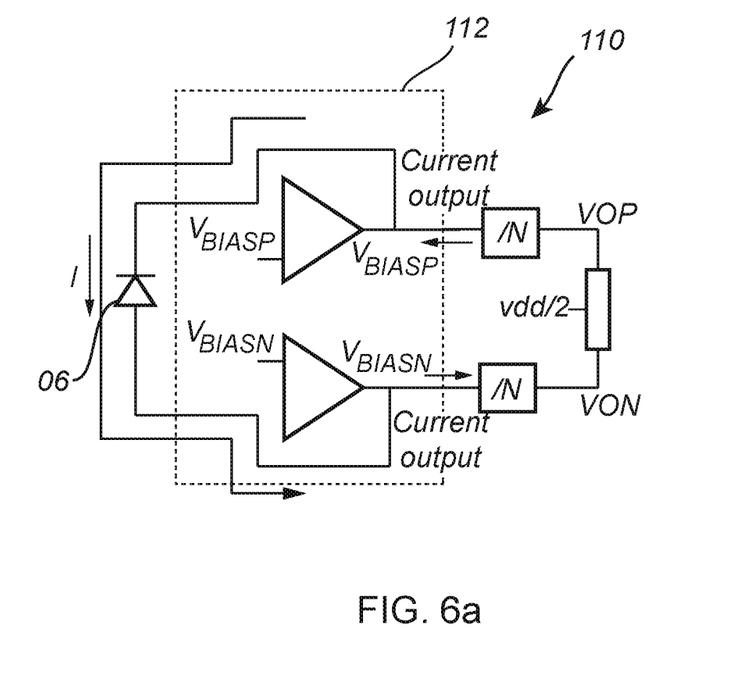
FIG. 6a is a schematic view illustrating signal levels in the read-out circuitry.
Figure 6B:
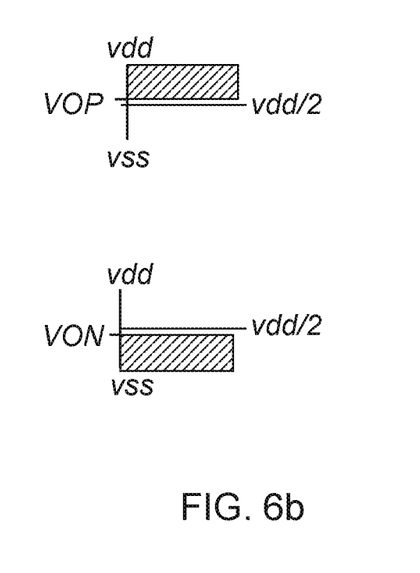
FIG. 6b is a schematic view illustrating a dynamic range of the read-out circuitry.

Referring now to FIGS. 6a-b, the large dynamic range provided by the read-out circuitry 110 is further explained.

As illustrated in FIG. 6a, the photodiode 106 is biased with a DC voltage ($V_{BIASP}$, $V_{BIASN}$) to generate current I through the photodiode 106. The input buffer stage 112 provides current output, and this differential current is down-converted to the load. This results in the output biasing points $V_{OP}$ and $V_{ON}$ smaller than $V_{BIASP}$ and $V_{BIASN}$, meaning a large dynamic range, as illustrated in the shaded areas in FIG. 6b, which illustrates the available output ranges in the read-out circuitry 110. Basically, when the output load is reduced, both biasing voltages and photodiode current are reduced.

In the above the inventive concept has mainly been described with reference to a limited number of examples. However, as is readily appreciated by a person skilled in the art, other examples than the ones disclosed above are equally possible within the scope of the inventive concept, as defined by the appended claims.

What is claimed is:

1. A device for read-out of a photoplethysmography (PPG) signal, said device comprising:
    a photodiode, which is configured to detect a PPG signal as intensity of light based on interaction of an emitted light signal with a blood flow of a subject, the photodiode comprising a first and a second terminal on opposite sides of the photodiode; and
    a read-out circuitry for reading out the PPG signal detected by the photodiode, the read-out circuitry comprising an input stage and an output stage;
    wherein the input stage is connected to receive a first input signal from the first terminal of the photodiode, a second input signal from the second terminal of the photodiode, and a DC bias voltage, and wherein the input stage is configured for current sensing to provide a fully differential amplification of the first input signal and the second input signal to a first current signal and a second current signal, and
    wherein the output stage is configured to receive the first current signal and the second current signal, wherein the first current signal and the second current signal comprise an AC component and a DC component of the PPG signal, and wherein the output stage is configured to generate a differential output voltage through a gain component.

2. The device according to claim 1, wherein the input stage comprises a first differential amplifier, which comprises a first and a second input of the first differential amplifier connected to receive the first input signal and the DC bias voltage, respectively, and which is configured to output an amplified signal to a first current sensor for generating the first current signal, and wherein the input stage comprises a second differential amplifier, which comprises a first and a second input of the second differential amplifier connected to receive the second input signal and the DC bias voltage, respectively, and which is configured to output an amplified signal to a second current sensor for generating the second current signal.

3. The device according to claim 2, wherein the first differential amplifier comprises a feedback loop connecting the first current sensor to the first input of the first differential amplifier, and wherein the second differential amplifier comprises a feedback loop connecting the second current sensor to the first input of the second differential amplifier.

4. The device according to claim 1, wherein the output stage comprises a first current source, which is controlled by the first current signal, and a second current source, which is controlled by the second current signal.

5. The device according to claim 1, wherein the gain component of the output stage comprises a resistor for providing a transimpedance amplifier mode of the output stage.

6. The device according to claim 1, wherein the gain component of the output stage comprises a capacitor for providing an integration mode of the output stage.

7. The device according to claim 1, wherein the output stage is configured to be selectively set in a transimpedance amplifier mode or an integration mode.

8. A wearable sensor for acquiring physiological information through a photoplethysmography, PPG, signal, the wearable sensor comprising:
    a carrier, which is configured to be worn by a subject; a light emitting diode, LED, which is configured to emit a light signal; and
    a device according to claim 1;
    wherein the carrier is configured to carry the LED and the device such that, when the carrier is worn by the subject, the LED is arranged to emit a light signal towards a skin of the subject and the photodiode of the device is arranged to detect the PPG signal as intensity of light based on interaction of the emitted light signal with a blood flow of the subject.

9. The wearable sensor according to claim 8, wherein the LED is configured to emit green light.

10. The wearable sensor according to claim 8, wherein the carrier is configured to carry the LED and the photodiode of the device such that, when the carrier is worn by the subject, the photodiode is configured to detect light emitted by the LED that is reflected by blood flow of the subject.

11. The wearable sensor according to claim 8, wherein the wearable sensor further comprises LED driving circuitry, which is configured to control the LED to emit pulsed light.

12. The wearable sensor according to claim 8, further comprising a processor, which is configured to receive a processor input signal based on the differential output voltage from the output stage of the read-out circuitry and which is configured to process the processor input signal for determining physiological information based on the processor input signal.

13. The wearable sensor according to claim 12, wherein the processor is configured to determine an estimated heart rate based on the PPG signal.

14. The wearable sensor according to claim 12, wherein the processor is configured to determine an estimated blood oxygen saturation.

* * * * *